United States Patent
Horsager et al.

(10) Patent No.: US 8,620,442 B2
(45) Date of Patent: Dec. 31, 2013

(54) MULTI-ELECTRODE INTEGRATION IN A VISUAL PROSTHESIS

(75) Inventors: Alan Matthew Horsager, Los Angeles, CA (US); Geoffrey M. Boynton, Seattle, WA (US); Ione Fine, Seattle, WA (US); Robert J. Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 338 days.

(21) Appl. No.: 13/014,968

(22) Filed: Jan. 27, 2011

(65) Prior Publication Data
US 2011/0184490 A1   Jul. 28, 2011

Related U.S. Application Data

(60) Provisional application No. 61/298,836, filed on Jan. 27, 2010.

(51) Int. Cl.
*A61N 1/18* (2006.01)
(52) U.S. Cl.
USPC ............... 607/53; 607/54; 607/118; 607/141
(58) Field of Classification Search
USPC ..................... 607/53, 54, 118, 141
See application file for complete search history.

(56) References Cited

U.S. PATENT DOCUMENTS

| 5,109,844 A | 5/1992 | de Juan, Jr. et al. |
| 5,935,155 A | 8/1999 | Humayun et al. |
| 6,400,989 B1 | 6/2002 | Eckmiller |
| 6,458,157 B1 | 10/2002 | Suaning |
| 2007/0198066 A1* | 8/2007 | Greenberg et al. ............ 607/53 |
| 2009/0306741 A1* | 12/2009 | Hogle et al. ................... 607/54 |
| 2009/0312818 A1* | 12/2009 | Horsager et al. ............... 607/54 |

* cited by examiner

*Primary Examiner* — Christopher D Koharski
*Assistant Examiner* — Natasha Patel
(74) *Attorney, Agent, or Firm* — Scott B. Dunbar (57) ABSTRACT

The present invention is a method of stimulating visual neurons to create the perception of light. A visual prosthesis electrically stimulating the retina with implanted electrodes exhibits interaction between electrodes stimulated closely together in both space and time. The method of the present invention includes determining a minimum distance at which spatiotemporal interactions occur, determining a minimum time at which spatiotemporal interactions occur, and avoiding stimulation of electrodes within the minimum distance during the minimum time. The minimum are ideally established for each individual patient. Alternatively, approximate minimums have been established by the applicants at 2 mm and 1.8 μsec.

11 Claims, 11 Drawing Sheets

| SUBJECT | EXPERIMENT | E1 | E2 | PHASE-SHIFT (ms) | $\beta$ | $\gamma$ | ERROR |
|---|---|---|---|---|---|---|---|
| | Theoretical | E1 | E2 | 0.075 | 1.0 | 0.00 | 0.000 |
| | Theoretical | E1 | E2 | 0.375 | 1.0 | −0.74 | 0.000 |
| | Theoretical | E1 | E2 | 1.8 | 1.0 | −1.00 | 0.000 |
| | Theoretical | E1 | E2 | 9.0 | 3.0 | −1.00 | 0.000 |
| S05 | 800 | C1 | D1 | 0.075 | 3.5 | −0.14 | 1.033 |
| S05 | 800 | C1 | D1 | 0.375 | 3.5 | −0.12 | 1.033 |
| S05 | 800 | C1 | D1 | 1.8 | 3.5 | 0.22 | 1.033 |
| S05 | 800 | C1 | D1 | 9.0 | 3.5 | 0.00 | 1.033 |
| S05 | 800 | A1 | A2 | 0.075 | 3.5 | 0.54 | 0.089 |
| S05 | 800 | A1 | A2 | 0.375 | 3.5 | 0.54 | 0.089 |
| S05 | 800 | A1 | A2 | 1.8 | 3.5 | 0.29 | 0.089 |
| S05 | 800 | A1 | A2 | 9.0 | 3.5 | 0.29 | 0.089 |
| S05 | 800 | C3 | C2 | 0.075 | 3.5 | 1.81 | 0.377 |
| S05 | 800 | C3 | C2 | 0.375 | 3.5 | 0.57 | 0.377 |
| S05 | 800 | C3 | C2 | 1.8 | 3.5 | −0.30 | 0.377 |
| S05 | 800 | C3 | C2 | 9.0 | 3.5 | 0.13 | 0.377 |
| S06 | 800 | C1 | B1 | 0.075 | 3.5 | 0.73 | 0.118 |
| S06 | 800 | C1 | B1 | 0.375 | 3.5 | 0.26 | 0.118 |
| S06 | 800 | C1 | B1 | 1.8 | 3.5 | −0.66 | 0.118 |
| S06 | 800 | C1 | B1 | 9.0 | 3.5 | −0.18 | 0.118 |

FIG. 4A

| SUBJECT | EXPERIMENT | E1 | E2 | PHASE-SHIFT (ms) | $\beta$ | $\gamma$ | ERROR |
|---|---|---|---|---|---|---|---|
| S06 | 800 | C3 | B2 | 0.075 | 3.5 | 0.18 | 0.962 |
| S06 | 800 | C3 | B2 | 0.375 | 3.5 | −0.29 | 0.962 |
| S06 | 800 | C3 | B2 | 1.8 | 3.5 | −0.52 | 0.962 |
| S06 | 800 | C3 | B2 | 9.0 | 3.5 | −0.64 | 0.962 |
| S06 | 800 | C2 | B2 | 0.075 | 3.5 | −0.18 | 0.856 |
| S06 | 800 | C2 | B2 | 0.375 | 3.5 | −0.14 | 0.856 |
| S06 | 800 | C2 | B2 | 1.8 | 3.5 | −0.47 | 0.856 |
| S06 | 800 | C2 | B2 | 9.0 | 3.5 | −0.48 | 0.856 |
| S06 | 800 | B3 | B2 | 0.075 | 3.5 | 0.12 | 0.351 |
| S06 | 800 | B3 | B2 | 0.375 | 3.5 | −0.32 | 0.351 |
| S06 | 800 | B3 | B2 | 1.8 | 3.5 | −0.82 | 0.351 |
| S06 | 800 | B3 | B2 | 9.0 | 3.5 | −0.71 | 0.351 |
| S06 | 800 | A4 | B4 | 0.075 | 3.5 | 0.04 | 0.425 |
| S06 | 800 | A4 | B4 | 0.375 | 3.5 | −0.32 | 0.425 |
| S06 | 800 | A4 | B4 | 1.8 | 3.5 | −0.56 | 0.425 |
| S06 | 800 | A4 | B4 | 9.0 | 3.5 | −0.75 | 0.425 |
| S06 | 800 | A1 | A2 | 0.075 | 3.5 | 0.80 | 0.476 |
| S06 | 800 | A1 | A2 | 0.375 | 3.5 | 0.55 | 0.476 |
| S06 | 800 | A1 | A2 | 1.8 | 3.5 | 0.20 | 0.476 |
| S06 | 800 | A1 | A2 | 9.0 | 3.5 | −0.64 | 0.476 |

FIG. 4B

| SUBJECT | EXPERIMENT | E1 | E2 | PHASE-SHIFT (ms) | $\beta$ | $\gamma$ | ERROR |
|---|---|---|---|---|---|---|---|
| S06 | 1600 | B2 | B4 | 0.075 | 3.5 | 2.16 | 0.286 |
| S06 | 1600 | B2 | B4 | 0.375 | 3.5 | 1.10 | 0.286 |
| S06 | 1600 | B2 | B4 | 1.8 | 3.5 | 0.84 | 0.286 |
| S06 | 1600 | B2 | B4 | 9.0 | 3.5 | 0.52 | 0.286 |
| S06 | 1600 | A2 | C2 | 0.075 | 3.5 | 0.25 | 0.341 |
| S06 | 1600 | A2 | C2 | 0.375 | 3.5 | 0.16 | 0.341 |
| S06 | 1600 | A2 | C2 | 1.8 | 3.5 | 0.22 | 0.341 |
| S06 | 1600 | A2 | C2 | 9.0 | 3.5 | 0.25 | 0.341 |
| S06 | 1600 | B3 | B1 | 0.075 | 3.5 | 0.88 | 0.079 |
| S06 | 1600 | B3 | B1 | 0.375 | 3.5 | 0.54 | 0.079 |
| S06 | 1600 | B3 | B1 | 1.8 | 3.5 | 0.19 | 0.079 |
| S06 | 1600 | B3 | B1 | 9.0 | 3.5 | 0.31 | 0.079 |
| S06 | 1600 | A1 | C1 | 0.075 | 3.5 | 1.30 | 0.411 |
| S06 | 1600 | A1 | C1 | 0.375 | 3.5 | 0.79 | 0.411 |
| S06 | 1600 | A1 | C1 | 1.8 | 3.5 | 0.05 | 0.411 |
| S06 | 1600 | A1 | C1 | 9.0 | 3.5 | −0.09 | 0.411 |
| S06 | 2400 | A1 | A4 | 0.075 | 3.5 | 0.99 | 0.269 |
| S06 | 2400 | A1 | A4 | 0.375 | 3.5 | 0.32 | 0.269 |
| S06 | 2400 | A1 | A4 | 1.8 | 3.5 | 0.28 | 0.269 |
| S06 | 2400 | A1 | A4 | 9.0 | 3.5 | 0.21 | 0.269 |
| S06 | 2400 | C4 | C1 | 0.075 | 3.5 | −0.88 | 7.212 |
| S06 | 2400 | C4 | C1 | 0.375 | 3.5 | 0.13 | 7.212 |
| S06 | 2400 | C4 | C1 | 1.8 | 3.5 | −0.76 | 7.212 |
| S06 | 2400 | C4 | C1 | 9.0 | 3.5 | −0.19 | 7.212 |

MULTI-ELECTRODE INTEGRATION IN A VISUAL PROSTHESIS

CROSS REFERENCE TO RELATED APPLICATIONS

This application claims priority to U.S. Provisional Application 61/298,836, filed Jan. 28, 2010, for Multielectrode Integration in a Visual Prosthesis, which is incorporated by reference.

GOVERNMENT RIGHTS NOTICE

This invention was made with government support under grant No. R24EY12893-01, awarded by the National Institutes of Health. The government has certain rights in the invention.

FIELD OF THE INVENTION

The present invention relates to visual prosthesis, and more particularly to apparatus and methods to compensate for integration of stimulation between geographically close electrodes.

BACKGROUND

Retinitis pigmentosa (RP) and age-related macular degeneration (AMD) are photoreceptor diseases that cause substantial vision loss and lead to subsequent blindness in over 15 million people worldwide. After the loss of the photoreceptor layer, the spatial organization of the inner nuclear and ganglion cell layers can become disorganized and inner nuclear and ganglion cell layers begin to thin. However, the inner nuclear and ganglion cell layers maintain relatively high cell density and some functional circuitry remains. These findings of residual function within the inner layers of the retina have inspired a variety of research focused on sight restoration technologies that interface with remaining retinal cells.

A great deal of progress has been made in treating one type of RP (i.e., Leber's Congenital Amaurosis; RPE65 mutation) using a gene replacement therapy. However, current gene therapies focused on restoring function within photoreceptors necessarily require the maintenance of photoreceptors and are specific to a single gene mutation gene mutation. This limits the utility of this approach for many types of RP since photoreceptor cells generally die off as a function of the disease process, and the genetics of RP is highly heterogeneous. Over 180 different gene mutations have been positively identified as being involved with photoreceptor disease and this number is likely an underestimate. One recent estimate is that there are likely to be over 400 gene mutations associated with photoreceptor disease.

A second approach to treatment is genetically targeting bipolar and/or ganglion cells with engineered photo-gates or light-sensitive proteins such as channelrhodopsin-2 (ChR2), which has the advantage of not needing to be specific to a given gene mutation. Still, ChR2 activation requires light stimulation levels that are 5 orders of magnitude greater than the threshold of cone photoreceptors and has a substantially limited dynamic range (2 log units). An ideal therapy would be able to treat blindness independent of the genetic mutation, in the absence of photoreceptors, and with reasonable response sensitivity.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Humayun, U.S. Pat. No. 5,935,155 describes the use of retinal tacks to attach a retinal array to the retina. Alternatively, an electrode array may be attached by magnets or glue. U.S. Pat. No. 5,109,844 to de Juan describes a flat electrode array placed against the retina for visual stimulation.

Any device for stimulating percepts in the retina must receive a signal describing a visual image along with power to operate the device. The device can not be powered by wires as any connection through the skin will create the risk of infection. Battery power is not practical as batteries are bulky and surgery is required to replace them. Such signal and power may be transmitted into the eye inductively as shown in Humayun U.S. Pat. No. 5,935,155. Humayun uses a primary (external) coil in front of the eye, possibly encased within the rim of a pair of glasses, and a secondary (internal) coil within the lens capsule or around the sclera just under the conjunctiva. Implanting within the lens capsule is difficult surgery and only allows for a small diameter coil. Larger coils are more efficient, can receive more power with less resulting temperature rise per unit of power received. Implanting around the sclera under the conjunctiva and near the surgical limbus (that is at the front of the eye) allows for a larger coil but may cause irritation or damage to the conjunctiva if the coil is placed in front near the cornea.

U.S. patent application Ser. No. 09/761,270, Ok, discloses several coil configurations including a configuration where the coil is offset about 45 degrees from the front of the eye. The offset configuration allows the primary and secondary coils to be placed closer together allowing for better inductive coupling. The bridge of nose partially blocks placement of a primary coil when placed directly in front of the eye.

A better configuration is needed allowing for close physical spacing of relatively large primary and secondary coils, without causing physical damages such as erosion of the conjunctiva.

Several groups have recently developed microelectronic retinal prostheses with the ultimate goal of restoring vision in blind subjects by stimulating the remaining retinal cells with spatiotemporal sequences of electrical pulses. Analogous to cochlear implants, these devices are designed to directly stimulate remaining retinal neurons with pulsing electrical current. To date, both semi-acute and long-term implanted devices have been demonstrated to be safe and capable of generating visual percepts in human subjects. Note, however, that only the Second Sight Argus trials have thus far allowed use of the system outside of the clinic in subject's daily lives. The ultimate goal of these projects is to generate useful vision in blind patients by presenting a spatial and temporal sequence of electrical pulses that represent meaningful visual information, such as a continuous video stream that uses electrical pulses rather than pixels.

Here we examine how systematic variations in spatiotemporal patterns of multi-electrode retinal stimulation influence the perceived brightness in our prosthesis patients. It is well known that for cochlear implants the precise timing of stimulation across electrodes has perceptual consequences as a result of both electrical field. However, to date, only limited data have been reported examining how electrodes interact during spatiotemporal stimulation in the retina. Earlier work from our group demonstrated significant interactions between pairs of electrodes, even when they are stimulated non-simultaneously. Here we systematically examined how these interactions affect perceived brightness and we present a simple computational model that describes these data.

SUMMARY OF THE INVENTION

The present invention is a method of stimulating visual neurons to create the perception of light. A visual prosthesis electrically stimulating the retina with implanted electrodes exhibits interaction between electrodes stimulated closely together in both space and time. The method of the present invention includes determining a minimum distance at which spatiotemporal interactions occur, determining a minimum time at which spatiotemporal interactions occur, and avoiding stimulation of electrodes within the minimum distance during the minimum time. The minimum are ideally established for each individual patient. Alternatively, approximate minimums have been established by the applicants at 2 mm and 1.8 μsec.

DETAILED DESCRIPTION OF THE PREFERRED EMBODIMENTS

Methods:

Subjects compared the brightness of a standard stimulus (where pulse trains across pairs of electrodes were synchronously presented) to the brightness of test stimuli (where pulse trains were phase-shifted by 0.075, 0.375, 1.8, or 9 ms). We measured the amount of total charge for each phase-shifted stimulus needed to make the test and the standard of equal brightness.

Results:

Depending on the electrode pair, interactions between electrodes could be either facilitatory (the amount of charge need to match the brightness of the standard summed across electrodes) or suppressive (more charge was needed to match the brightness of the standard than would be required for either individual electrode alone). Data were fit with a simple, 2-parameter model. The amount of interaction between electrodes decreased both as a function of increasing time (phase-shift between pulse trains) and space (center-to-center distance between the electrode pair).

Conclusions:

During multi-electrode stimulation, interactions between electrodes have a significant influence on subjective brightness that can be either facilitatory or suppressive. These interactions can be described using a simple computational model that has provided some insight into the underlying electrical and neural mechanisms responsible for spatiotemporal integration during multi-electrode stimulation of the human retina.

Materials & Methods

Figure 1A:
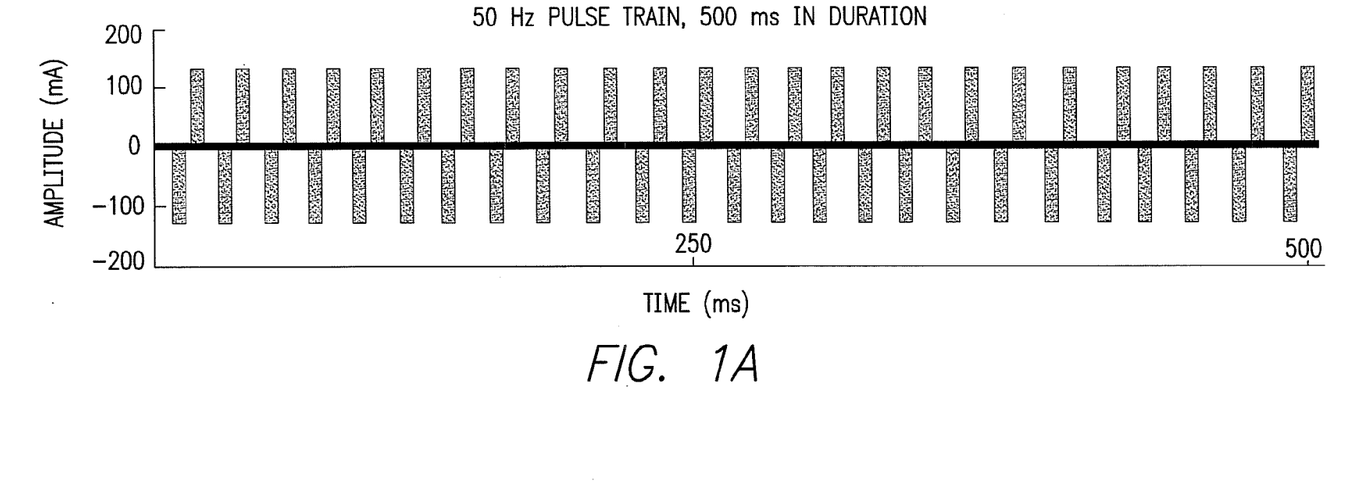
FIG. 1A depicts a pulse train for neural stimulation
Figure 1B:
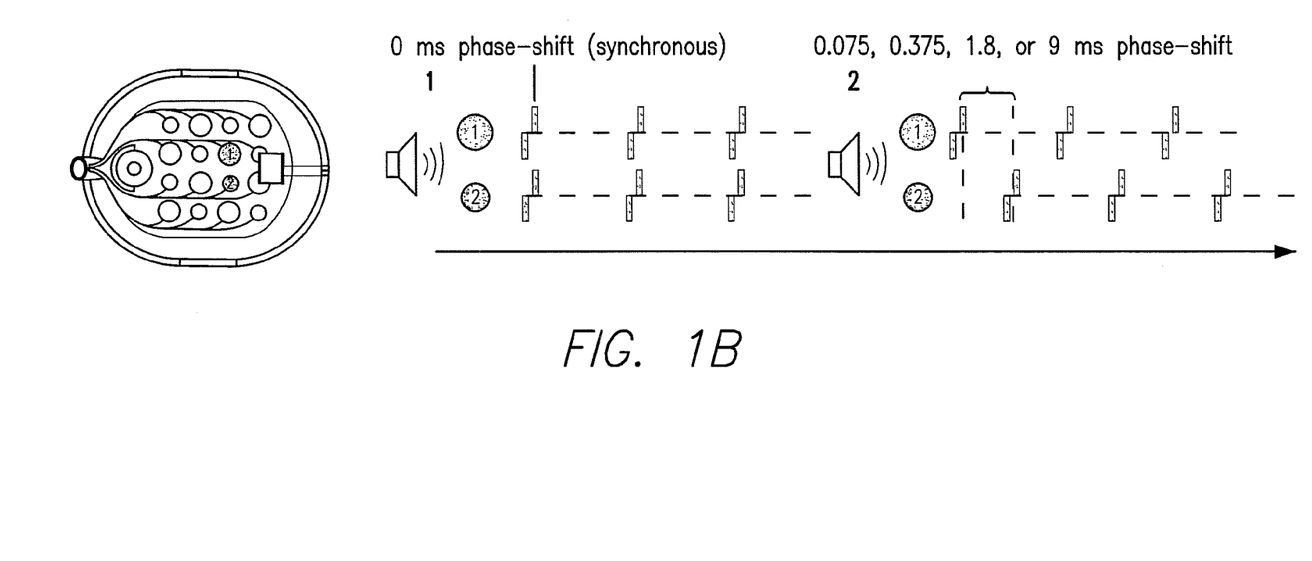
FIG. 1B depicts phase shifted pulse trains for neural stimulation.
Figure 9:
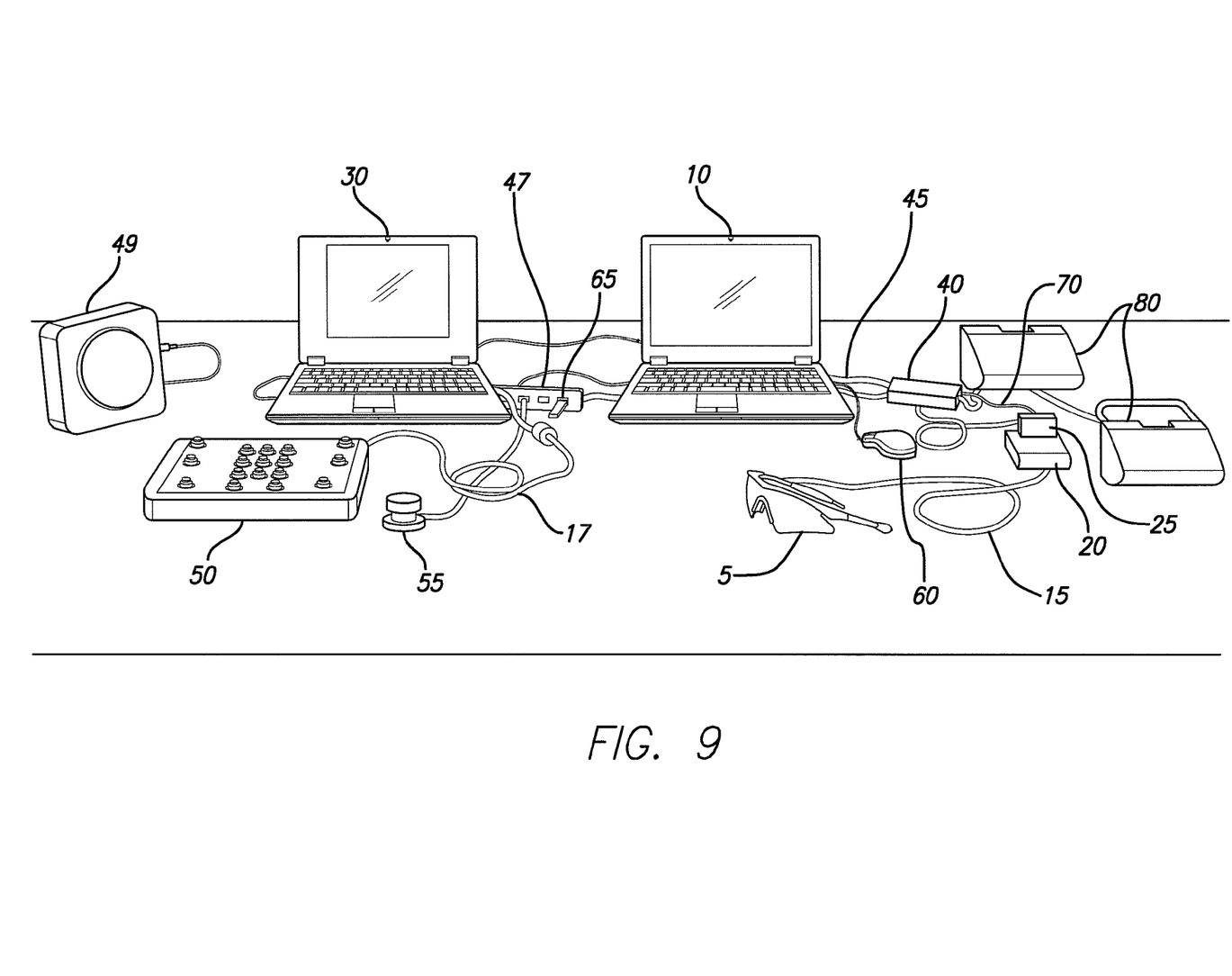
FIG. 9 shows the components of a visual prosthesis fitting system.

Referring to FIG. 1 Stimuli were programmed using Matlab® on a PC, which then communicated parameters to an external Visual Processing Unit (see FIG. 9). Power and signal information could be independently controlled for each electrode. In FIG. 1A (Pulse train) stimulation on each electrode was a 50 Hz pulse train that was 500 ms in duration. Unless otherwise noted, the cathodic and anodic phases or each biphasic pulse was 0.45 ms in duration, with a 0.45 ms interphase delay. In FIG. 1B (Brightness matching task) subjects compared the brightness of a standard (1) and test (2) stimulus. The timing of pulses across the two electrodes was time-synched (phase-shifted by 0 ms) in the case of the standard. The test stimulus was identical to the standard except there was a phase-shift between pulses across electrodes.

To develop the experimental data, subjects were implanted, epiretinally, with an array of disk electrodes in the macular region. Electrodes were either 260 or 520 micrometers (μm) in diameter, arranged in an alternating checkerboard pattern with 800 μm center-to-center separation between each electrode.

Psychophysical Methods

All pulse waveforms consisted of biphasic, cathodic-first, charge-balanced square wave pulses, presented as trains of pulses (FIG. 1A). For safety reasons, all individual pulses within a pulse train were charge-balanced. Here, we used cathodic and anodic pulses of equal width (0.45 ins, unless otherwise noted), with the cathodic phase presented first. Each biphasic pulse within the pulse train contained a 0.45 ms interphase delay between cathodic and anodic phases. Pulse trains were 500 ms in duration at a rate of 50 Hz. All stimuli were presented in photopic conditions.

Subjective Brightness Matching During Paired-Electrode Stimulation.

Subjective brightness matching was carried out within a given electrode pair using a two-interval, forced-choice procedure. Each trial contained two temporal intervals. One interval always contained synchronized pulse trains across the pair of electrodes. The amplitudes of these synchronized pulse trains were set to 1.5, 2, 2.5, or 3 times the perceptual threshold of each electrode in the pair.

The other interval contained pulse trains that were phase-shifted by 0.075, 0.375, 1.8, or 9 ms. At our stimulation frequency (50 Hz), a 9 ms phase-shift resulted in perfectly interleaved pulses across a pair electrodes, as shown in FIG. 1B). The order of presentation of the two temporal intervals was randomized, and subjects were asked to report which interval contained the brighter stimulus. In most conditions pulse trains were presented on both electrodes in the pair. A one-up, one-down staircase method was used to adjust the amplitude of the phase-shifted pulse trains based on the observer's response. For example, if the observer responded that the test phase-shifted stimulus was brighter than the standard time-synched stimulus, the amplitude of the phase-shifted pulse trains was decreased by a fixed amount of charge. Depending on the condition, the increase or decrease in charge was applied to both electrodes in the pair or to only one of the two electrodes. We also compared the brightness of the standard time-synched electrode pair to test stimuli consisting of just one of the two electrodes in the pair.

Each brightness match was based on a minimum of 100 trials. A cumulative normal was used to find the point of subjective equibrightness, and error bars were estimated using an adaptive sampling Monte-Carlo simulation. Each individual psychometric function was inspected to make sure that an adequate fit was obtained, and data was recollected if fits were inadequate (based either on the estimated error or visual inspection).

Stimulus Set.

Figure 3A:
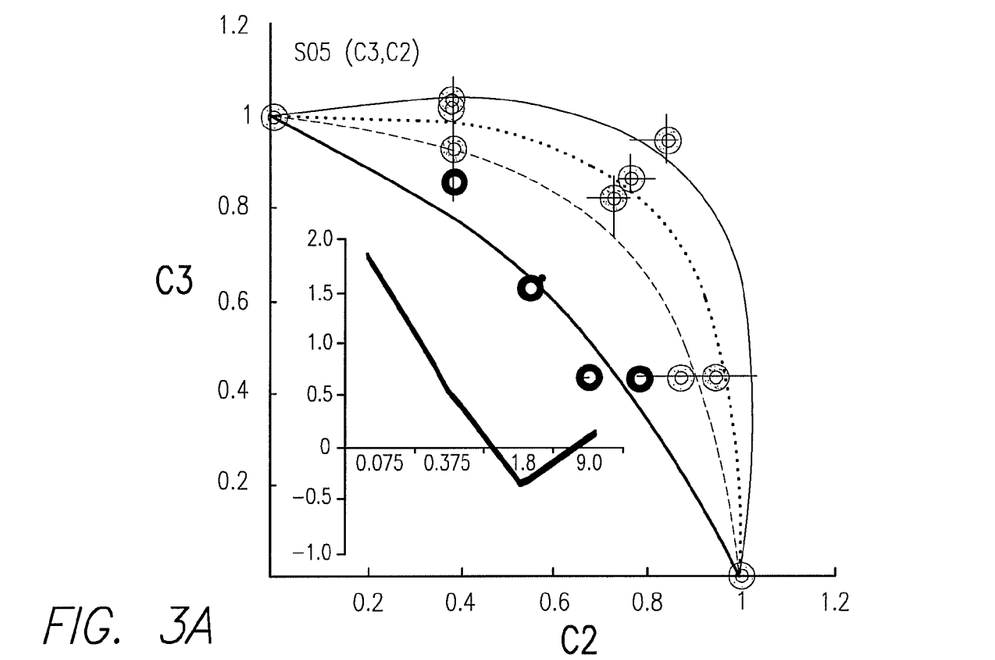
FIG. 3 is a set of graphs depicting charge required to match the brightness of the standard stimulus, each curve representing a different phase sift.
Figure 3B:
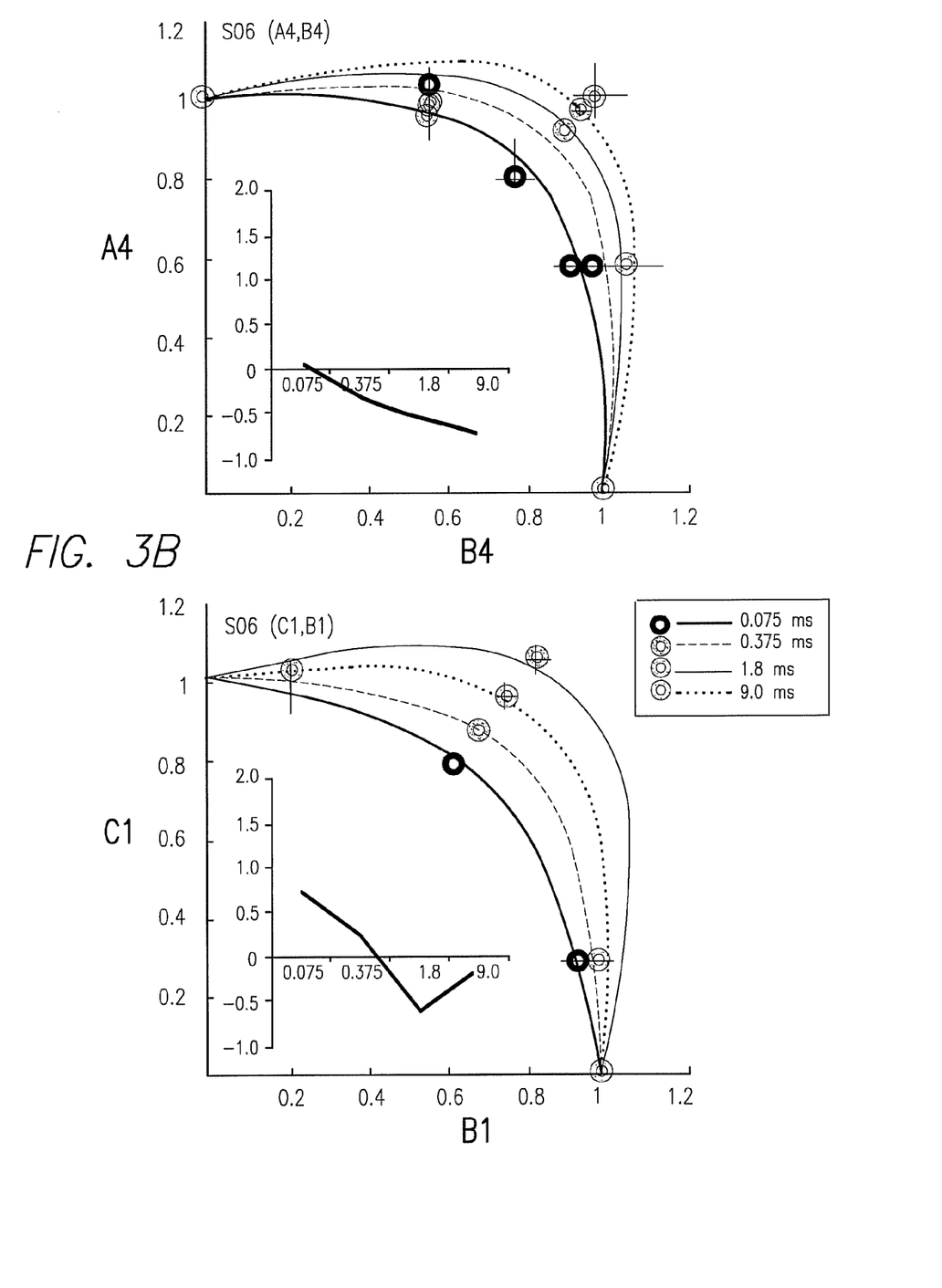

Referring to FIG. 3, data for electrodes separated by 800 μm was collected on a total of 13 electrode pairs across subjects. 4 and 3 electrode pairs were measured for electrodes separated by 1600 and 2400 μm distances, respectively. The results are shown in table 1, FIGS. 4a and 4b.

The only criterion used to choose the electrode pairs used in these experiments was that single pulse thresholds were relatively low on both electrodes in the pair. This allowed us to collect suprathreshold data across a range of brightness levels while remaining within charge safety limits. Given this constraint, electrodes were then chosen that were distributed as evenly as possible across the array.

For each phase-shift, we measured the current necessary to match the brightness of a standard pulse consisting of pulses presented simultaneously on E1-E2. Five different test stimuli were used: 1) E1 only, 2) E2 held fixed and E1 adjusted, 3) E1 and E2 adjusted simultaneously, 4) E1 held fixed and E2 adjusted, and 5) E2 only. The obtained amplitude values for electrodes E1 and E2 at the point of brightness match were normalized by the amplitude required to match the brightness of the test stimulus using only the E1 or E2 electrode, respectively. Example data sets are shown in FIG. 3. The data presented here represent testing sessions that occurred on roughly a weekly basis (~3 hours per session) over the course of 2 years.

Model of Spatiotemporal Integration

Data were fit using the following model:

$$B_\tau = E_1^\beta + E_2^\beta + \gamma_\tau E_1 E_2 \qquad \text{eq. 1}$$

where $B_\tau$ is the brightness of the percept generated by the given stimulation pattern on the electrode pair, $\tau$ represents the delay in stimulation between the two pulses, and $E_1$ and $E_2$ are the normalized current amplitudes on each of the two electrodes in the pair (charge needed to match the brightness of the standard divided by the charge needed to match the brightness of the standard using $E_1$ or $E_2$ alone). The free parameter $\gamma_\tau$ can be thought of as representing the mutual interaction between $E_1$ and $E_2$. $\beta$ can be thought of as representing the nonlinear increase in brightness as a function of the amount of current for electrodes $E_1$ and $E_2$.

Figure 2:
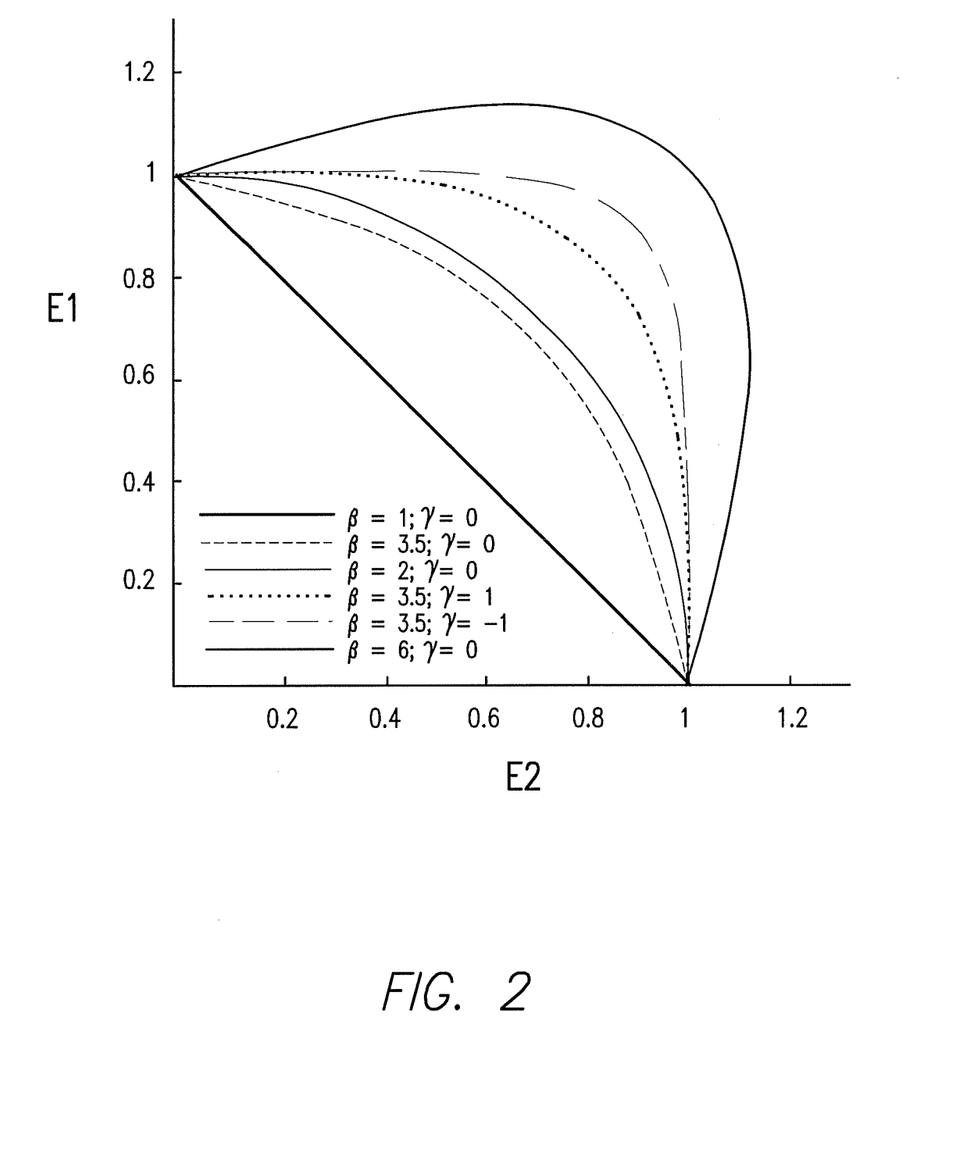
FIG. 2 depicts a graph of theoretical fit models.

FIG. 2 (A) Theoretical model outputs. The data above is theoretical and is an example of how the model output varied as a function of the parameters $\gamma$ and $\beta$. The lines represent model fits using a range of parameters.

FIG. 2 illustrates example model fits. The x and y axes represents normalized charge for electrodes E1 and E2, and each line represents model fits for six different parameter values of $\gamma$ and $\beta$. The solid black curve represents the simplest case, linear integration, or perfect summation ($\beta=1$ and $\gamma=0$). In this case apparent brightness sums linearly across both electrodes in the pair. The gray dashed-dot curve is an example of perfect independence where brightness is essentially determined by whichever of the two electrodes appears brightest. Note that, since the values of E1 and E2 are always less than or equal to 1, the interaction term $\gamma_\tau$ has very little effect on the final output when $\beta$ is large. The red, green and blue lines represent three intermediate conditions. The red line represents $\beta=3.5$, $\gamma=0$, the green line represents $\beta=2$, $\gamma=0$, and the blue line represents $\beta=3.5$, $\gamma=1$. Note that the effect of increasing the interaction between the two electrodes is very similar to reducing the value of $\beta$. The dashed gray curve represents an example of mutual suppression between electrodes ($\beta=3.5$, $\gamma=-1.0$) resulting in a bowing out of the curve beyond the boundary of x<=1, y<=1. In other words the amount of current needed to match the brightness of the standard is greater than is required for either electrode stimulated in isolation.

When fitting data we treated all four delays as part of the same data set. For each delay we generally collected three data points. With the end-points (which were constrained to fall on x=1, y=0 and y=0, x=1), this meant that there were in total 12 data points within each data set.

Our assumption was that $\beta$ can be thought to represent the nonlinear increase in brightness as a function of the amount of current and $\gamma$ represents mutual interaction between electrodes. As described above, changes in $\gamma$ and $\beta$ trade off against each other in "bowing" the curves. This meant that, if $\gamma$ and $\beta$ were fit simultaneously the model was under-constrained—while we obtained a fairly well-defined curve representing changes in $\gamma$ as a function of delay for each electrode pair, our function minimization procedure tended to converge on a fairly arbitrary value of beta which was compensated for by an absolute shift across all the obtained $\gamma$ values. We therefore held $\beta$ fixed at a value of 3.5 for all delays. This fitting process resulted in a model with 4 free parameters Results Subjects typically reported that phosphenes appeared white or yellow in color, and were round or oval in shape. At suprathreshold, percepts were reported as brighter and the perceived shape occasionally became more complex than a simple circle or oval. For single electrode stimulation, shapes were reported as being approximately 0.5-2 inches in diameter at arm's length, corresponding to roughly 1-3 degrees of visual angle.

When stimulation was presented on electrode pairs, the percept was generally of a larger area of relatively uniform brightness which was reported to appear to be approximately 2-4 inches in length or width at arm's length, corresponding to roughly 3-6° of visual angle. Occasionally, a dark percept rather than a white or yellow percept was reported. In this case, the patient would use the relative contrast of the percept for subjective brightness comparison. We did not see any systematic differences in threshold or slopes of the brightness matching psychometric functions between light or dark percepts. The complexity of the stimulus was greater than with single electrodes: generally consisting of multiple phosphenes. It should be noted that these phosphene patterns did not necessarily align with the map of activated electrodes: i.e. the percept elicited by a 2×2 array of activated electrodes did not necessarily map neatly onto a 2×2 array of visual percepts in the expected location in space. Synchronous, pseudo-synchronous, and asynchronous stimuli were generally perceived as spatially identical, and only differed in perceived temporal properties (i.e. flicker) for the relative low pulse frequency of 20 Hz, which, as reported earlier, is likely to be near subjects' limit for perceivable flicker.

In the brightness matching task, subjects were asked to ignore all aspects of the percept other than brightness/contrast. As described above, percepts could either be single or multi-phosphene percepts. In multi-phosphene percepts, subjects were asked to average the brightness across all phosphenes. The obtained psychometric functions for these brightness matches suggest that subjects were able to perform the task quite easily.

Subjective Brightness and Pulse Timing Across Electrodes

Referring to FIG. 3, normalized charge required to match the brightness of the standard stimulus. Each curve represents a different phase-shift in the test stimuli. All electrodes shown here are separated by 800 μm. The data points plotted for 0.075, 0.375, 1.8, and 9.0 ms phase-shifts are represented by black, dark gray, medium gray, and light gray circles, respectively. Model fits for each of the different phase-shifts are solid, dash-dotted, dashed, and dotted lines of the same color. (A-B) Two electrode pairs are shown. Gamma values ($\gamma$ are plotted (inset) as a function of phase-shift for each model fit. As shown in FIG. 3, interactions varied considerably across electrode pairs: here we show examples of different kinds of interaction.

Generally, the amount of charge required to match the brightness of the standard increased as a function of phase-shift, as represented by the curves "bowing out" further from the line x=y as a function of phase-shift in Panels A and B.

The inset graphs of each panel represent $\gamma$ as a function of phase-shift. As described above, $\gamma$ and $\beta$ trade off against each other in "bowing" the curves. With $\beta$ fixed at a value of 3.5, we found that values of $\gamma$ decreased as a function of delay (See FIGS. 3 and 4 insets), though curves shifted up or down the $\gamma$-axis depending on the electrode pair. The drop in $\gamma$ as a function of delay suggests a general progression from facilitatory interactions towards independence as a function of delay. In some electrode pairs, longer delays led to suppressive interactions as represented by negative values of gamma (and the curves describing interactions between electrodes bowing out beyond x=1, y=1).

The curve for the 0.075 phase-shift generally overlapped the data point representing the standard stimulus (where the pulses were presented simultaneously). There was also little difference in the curves representing 1.8 and 9 ms phase shifts, suggesting that the interactions between electrodes within this dataset begin to asymptote by 1.8 ms.

It might be expected that, since the size of the current field increases as a function of increasing current amplitude, there might be an increase in the spatiotemporal interactions at higher amplitudes (or for stimuli which were further above threshold). An increase in spatiotemporal integration would be thought to result in higher values of $\gamma$. However, we found no effect of pulse amplitude on spatiotemporal integration. Similar integration values were found for stimuli at threshold, 1.5× threshold, and 2-3× threshold. There was no statistical difference between these 3 different conditions using a two-way ANOVA (electrode x condition, $p>0.05$). On 4 pairs of electrodes, we tested all three conditions (threshold, 1.5×, 2×, and 3× threshold). When we limited our statistical analysis to those electrodes (paired single tailed t-test, $p>0.05$) we still found that interactions were no larger for stimuli that were further above threshold.

Figure 4A:
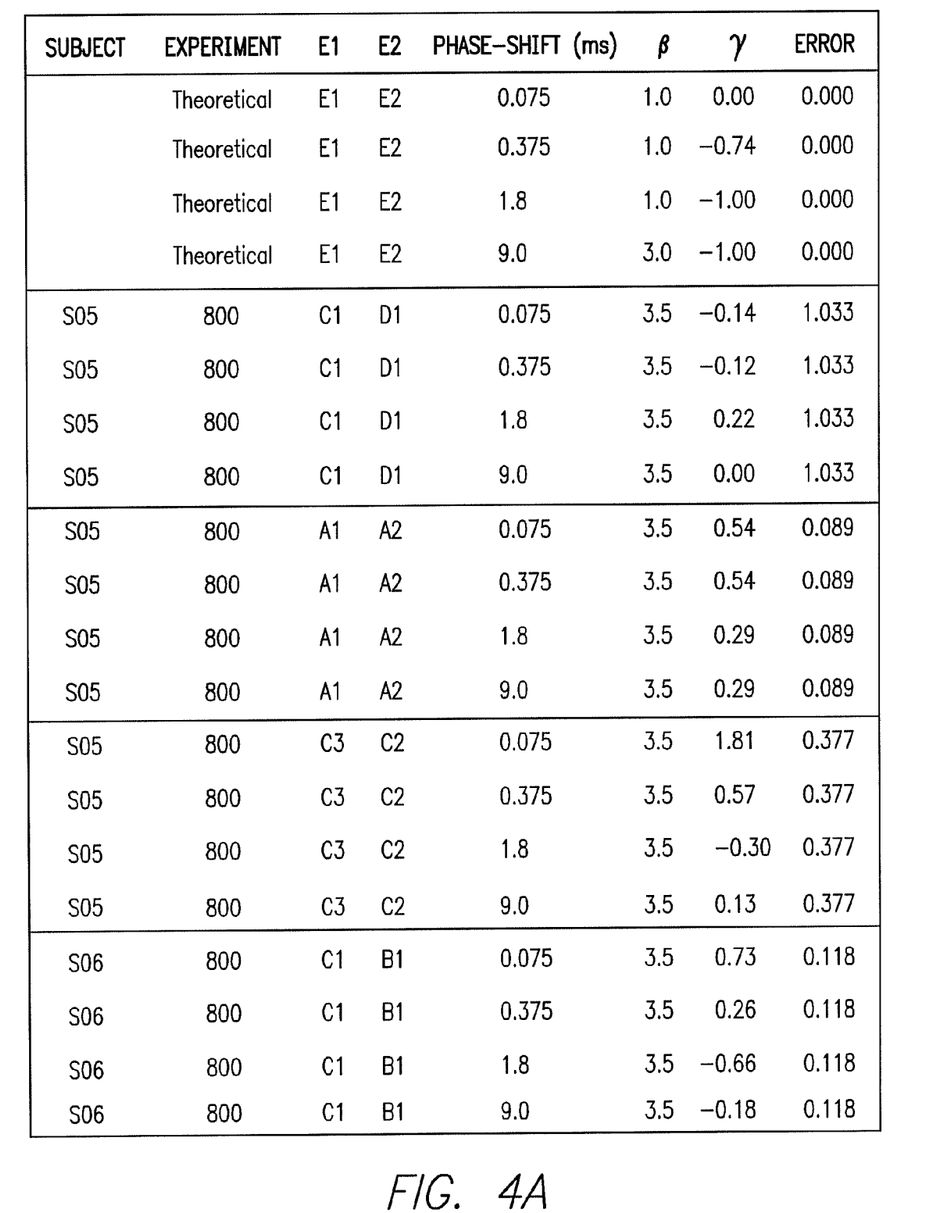
FIG. 4a and FIG. 4b (Table 1) form a data table of phase shift effects both theoretical and measured.
Figure 4B:
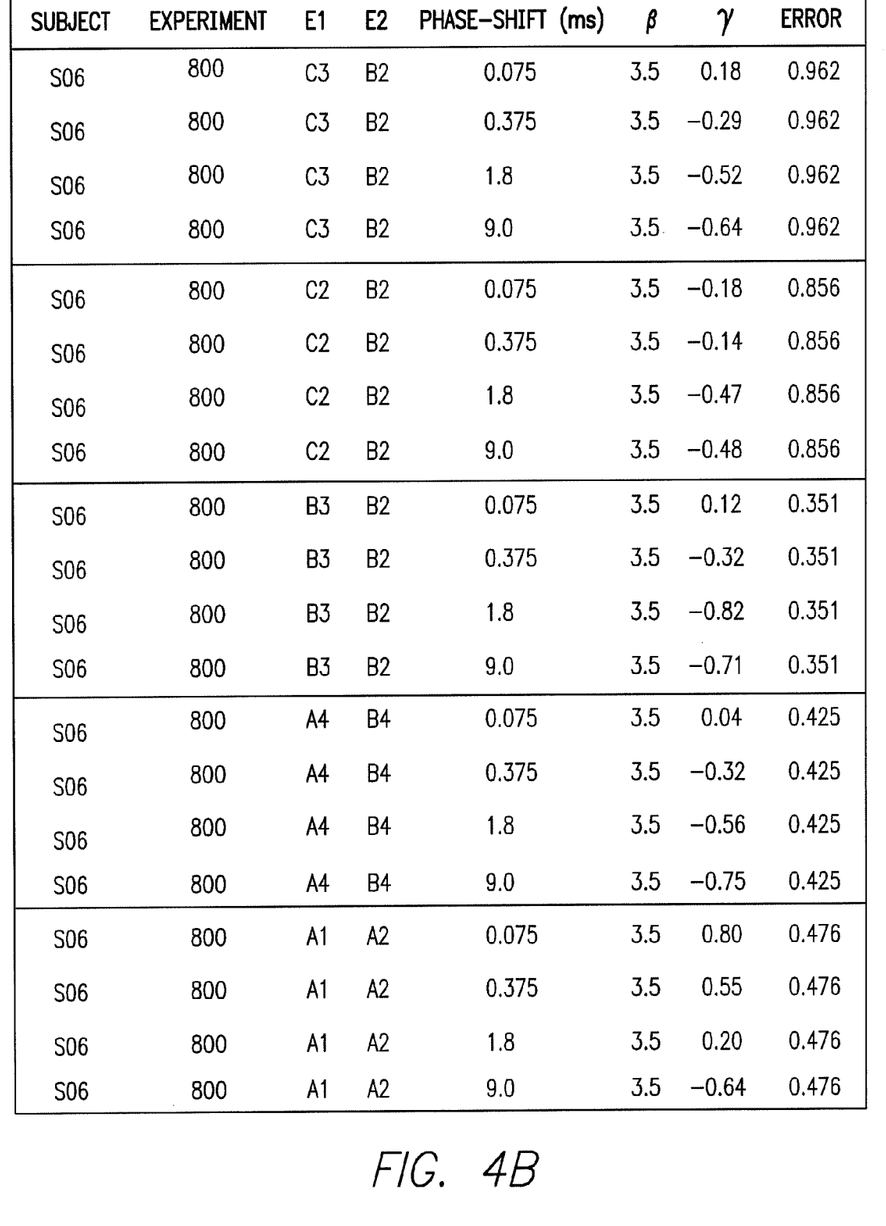

Referring to FIGS. 4A and 4B (Table 1), parameter values for model fits for all electrode pairs. Column 1 is the subject being evaluated, Column 2 shows the brightness of the standard and the electrode distance. Column 3 lists the electrodes being evaluated. Column 4 lists the phase-shift. Column 5 and 6 are the $\gamma$ and $\beta$ parameter values. Column 8 shows the error values of the model fits.

Figure 5A:
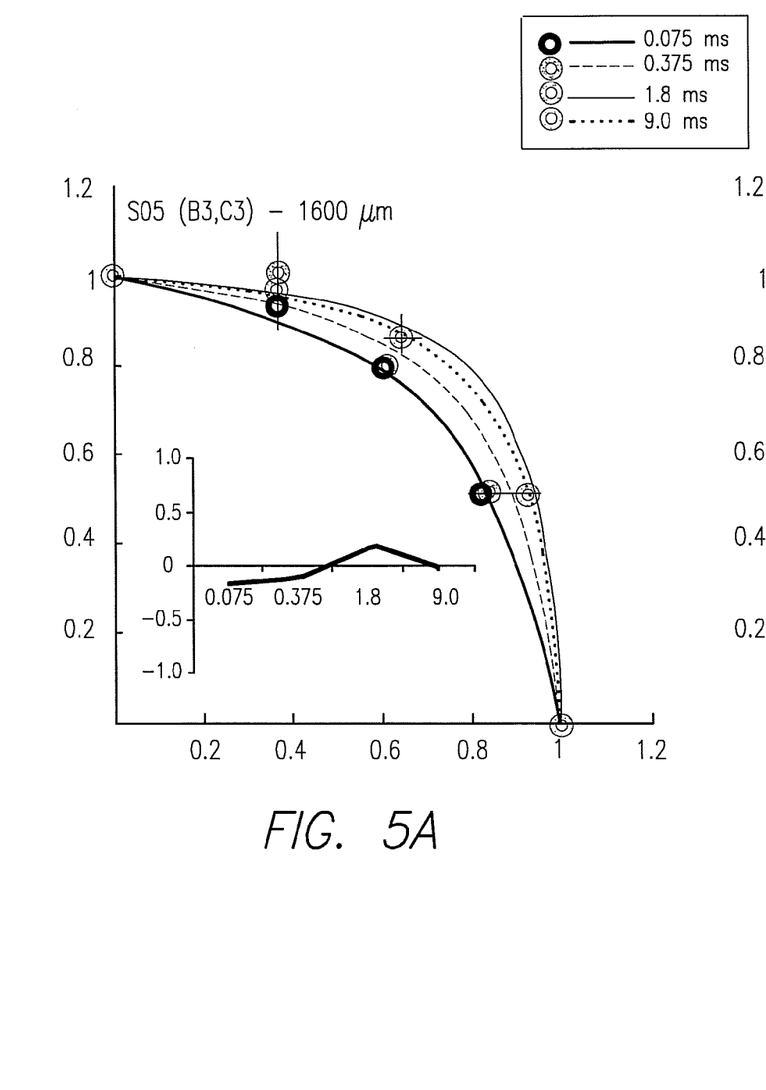
FIG. 5 is a pair of graphs depicting data and model fits for electrode pairs separated by 1600 and 2400 μm.
Figure 5B:
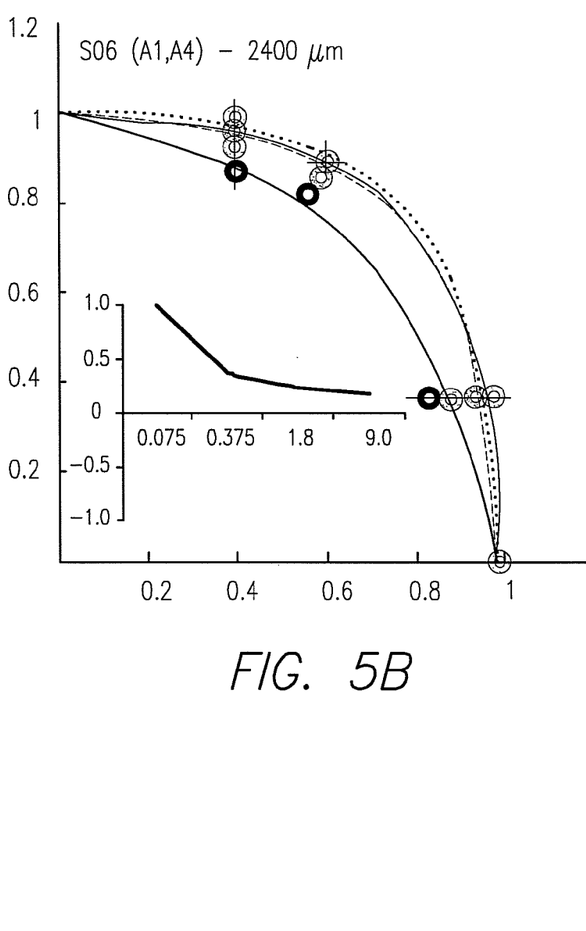

Referring to FIG. 5, normalized charge to maintain equibrightness as a function of phase-shift between pulses across 1600 and 2400 μm separated electrodes. The data points plotted for 0.075, 0.375, 1.8, and 9.0 ms phase-shifts are represented by black, dark gray, medium gray, and light gray circles, respectively. The model fits for each of the different phase-shifts are solid, dash-dotted, dashed, and dotted lines of the same color. (A) One electrode pair for subject S06 at 1600 μm. (B) One electrode pair for subject S06 at 2400 μm separation. Gamma values ($\gamma$ are plotted (inset) as a function of phase-shift for each model fit.

FIG. 5 shows data and model fits for electrode pairs separated by 1600 and 2400 μm. We fit these data with same model as was used for the 800 μm separated data. Two example electrode pairs (one at 1600 and the other at 2400 μm separation). The values of the parameter $\gamma$ are plotted in the inset graphs as a function of phase-shift in each 1600 and 2400 μm separated condition. The parameter values for the 1600 and 2400 μm separated electrodes are reported in FIG. 6 (Table 2).

Figure 6:
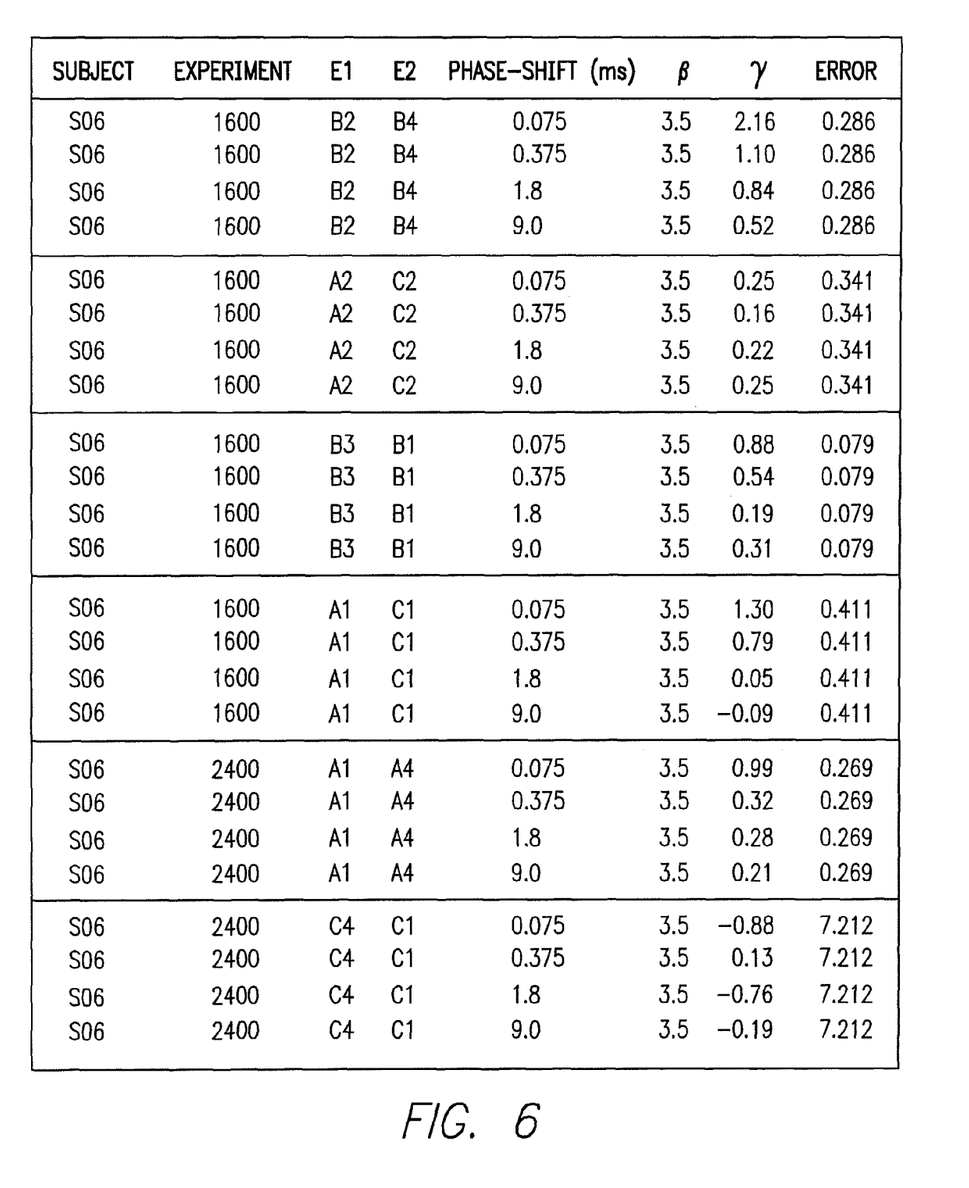
FIG. 6 (table 2) Parameter values for model fits of the various 1600 and 2400 μm separated electrode pairs.

Referring to FIG. 6 (Table 2), parameter values for model fits of the various 1600 and 2400 μm separated electrode pairs. Column 1 is the subject being evaluated, including the theoretical data plotted in FIG. 2. Column 2 is the distance between the electrode pairs being evaluated. Column 3 & 4 are the electrodes being evaluated. Column 5 is the phase-shift. Column 6 and 7 are the $\gamma$ and $\beta$ parameter values. Column 8 is the error value of the model fits.

Earlier work of ours demonstrated significant interactions between pairs of electrodes, even when stimulated non-simultaneously. Here we examined how these interactions affect perceived brightness. We measured the perceptual change in brightness as a function of the temporal separation between suprathreshold electrical pulses across pairs of electrodes.

The data described here demonstrate that when more than one electrode is stimulated over time, the percept that is generated is not independent from neighboring electrodes. Even when electric fields are not overlapping in time, there are still neural spatiotemporal mechanisms of integration. In this data set the effects of these interactions only seem to begin to asymptote when pulses are separated by approximately 1.8 ms. This time course is compatible with a number of physiological substrates. One possibility is that local differences in brightness are mediated by neural populations that lie between, and receiving stimulation from, more than one electrode. Such neural populations would integrate information from both pulse trains. Previously, we carried out multiple experiments and found no reason to assume that any other factor played a major role in determining spatiotemporal interactions.

As with the data presented earlier, we found that spatiotemporal interactions decreased with electrode separation. However we did find some interactions even between electrodes separated by more than 2 mm on the retina. The electrodes in our display differ in their height from the retinal surface, which presumably means that the extent of current spread on the retinal surface is different across electrodes.

Another possibility is that these long-range interactions are mediated by lateral connections in the retina. Recent evidence suggests very fine temporal sensitivity within lateral connections mediated by wide-field amacrine cells. These connections can span up to many millimeters within the retina. These connections therefore have the spatial and temporal qualities that would be required to influence our subjects' ability to discriminate between patterns differentiated by extremely fine temporal information across relatively wide regions of space within the retina.

Finally, it is possible that these interactions may be mediated by cortical sensitivity to precise timing patterns across space. Stimulation using extremely short pulses (~0.1 ms) results in precise single spikes within ganglion cells that are phase-locked to the pulses with a precision of <0.7 ms, and presynaptic-driven spiking is abolished with stimulation frequencies above 10 Hz. If this precise timing information is passed from retina to cortex, as suggested by data showing behavioral adaptation to very high temporal frequencies, it is possible that the sensitivity to pulse timing across electrodes is the result of a cortical mechanism sensitive to spatiotemporal firing patterns originating in the retina.

Modeling percepts would be much more computationally simple if the brightness of percepts did not interact nonlinearly across electrodes. However, the interactions described here do offer the potential for significant perceptual flexibility. Simply by altering the relative timing of stimulation, it is possible to vary the brightness elicited by a pair of electrodes.

While interactions between electrodes were generally facilitatory at short phase delays, and became more independent, or even suppressive, at longer phase delays, there was significant variability across electrode pairs. The reason for this variability is not clear: we saw no clear relationship between the spatiotemporal interactions described here and electrode to tissue distances or the position of electrode pairs with respect to the macula, though our dataset was limited, and cannot exclude the possibility these two factors might play a role. Other possible sources of this variation between electrode pairs might include inhomogeneities in retinal rewiring or degeneration across the retinal surface.

Although this variation across electrode pairs means that working out what factors impact spatiotemporal interactions across electrodes is likely to be a major concern for retinal prosthesis development, it should be noted that we were able to create a model to represent these interactions which required relatively few free parameters per electrode pair. Indeed, for a given overall brightness level (across both electrodes) and phase-delay, interactions can be described using a single free parameter. Although it is certainly the case that the model fits described here can be improved upon with more complex models, the simplicity of our model has the advantage that it would require a relatively small amount of data to be collected to estimate the necessary parameters—indeed for a fixed phase shift and brightness level only a single measurement would be necessary. As a result, simple 'approximation models' such as that described here may be of more practical use when designing stimulation protocols that involve multi-electrode arrays than more complex models. Given earlier work by our group showing that apparent brightness can be described as a power function of stimulation intensity it is likely that such models will extend relatively straightforwardly towards describing spatiotemporal interactions across multiple brightness levels.

Previous studies on these patients by our group has demonstrated that it is possible to model perceived brightness as a function of electrical stimulation on a single electrode across a wide variety of timing configurations. The model described here is a further step towards showing that it should be possible to predict the perceived brightness for different regions of an array of percepts generated by a two-dimensional electrode array with relatively simple models. Such models are of course necessary to accurately represent a visual scene is that is constantly changing both in space and time.

Figure 7:
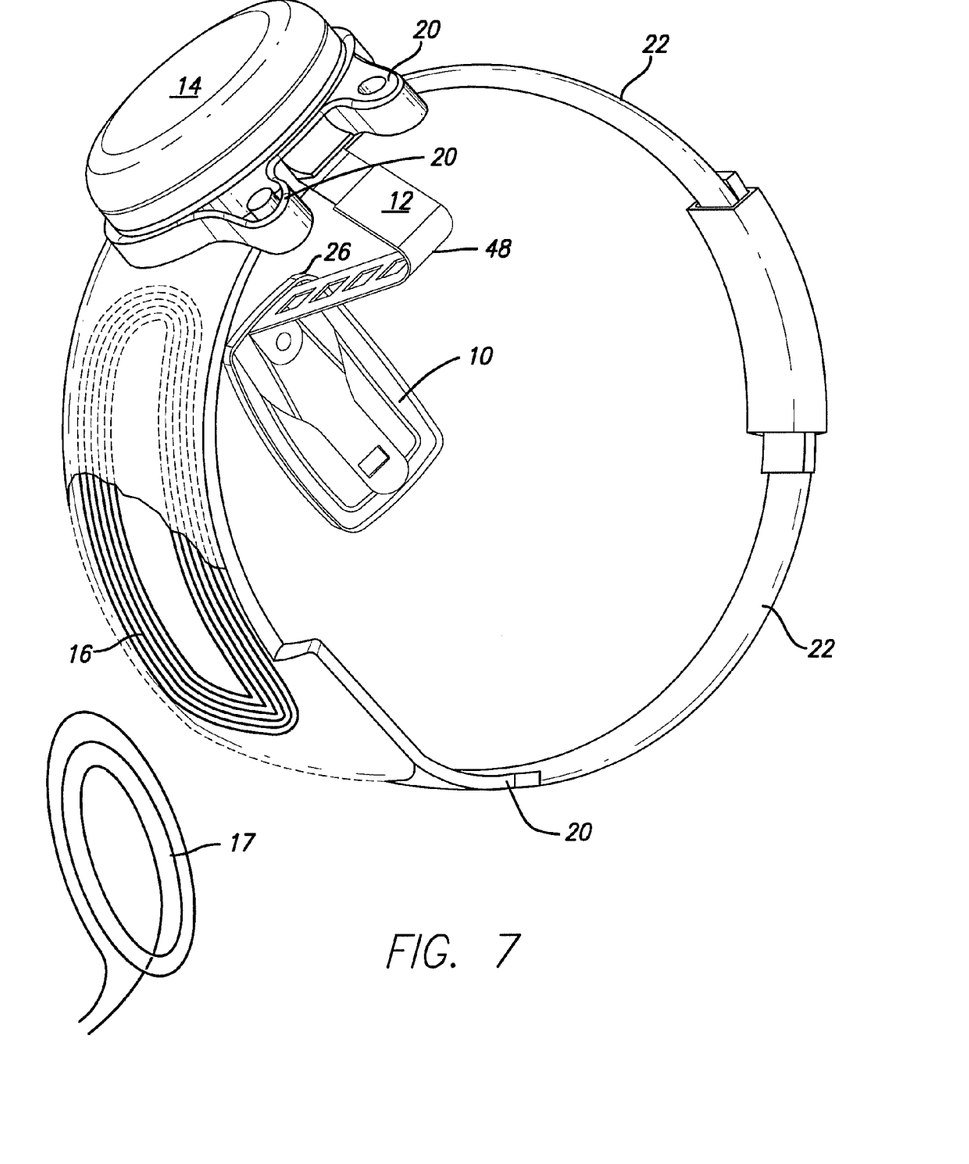
FIG. 7 is a perspective view of the implanted portion of the preferred visual prosthesis.
Figure 8:
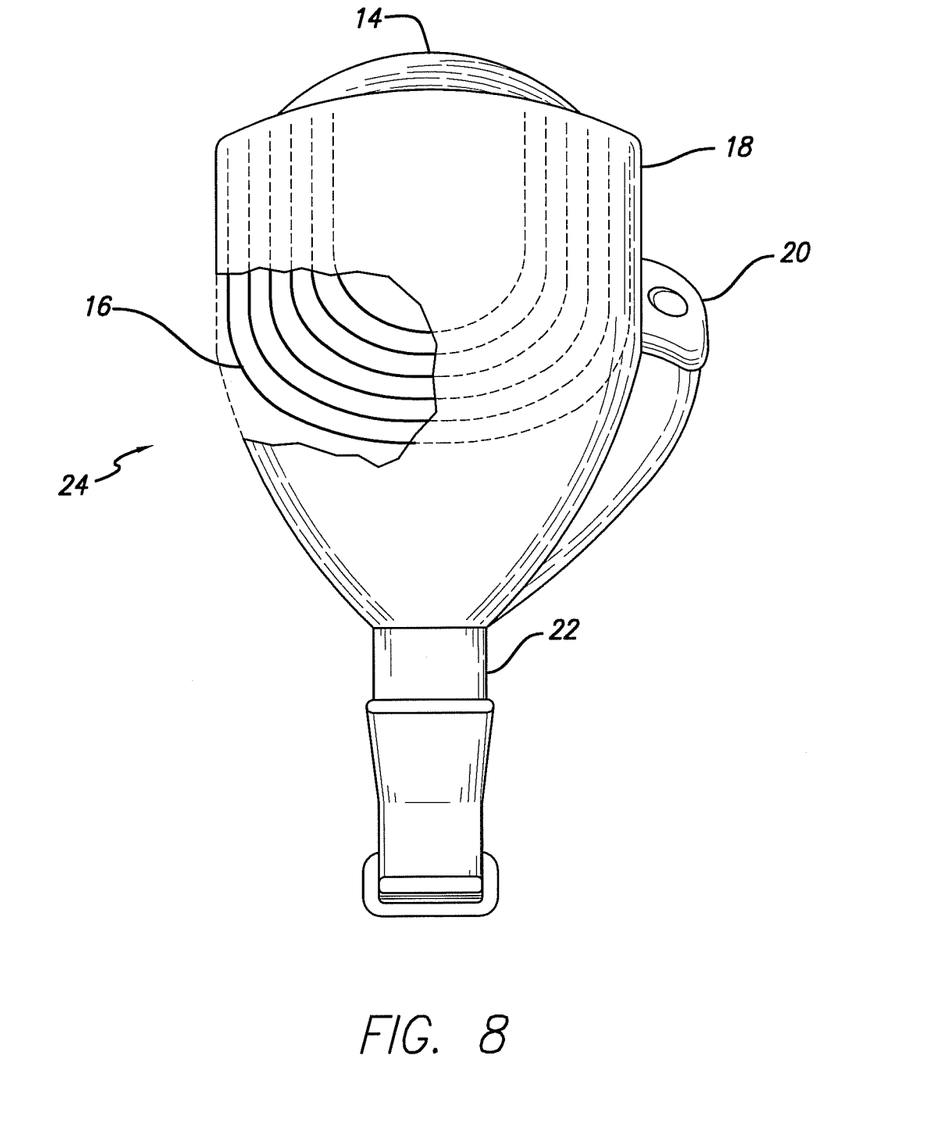
FIG. 8 is a side view of the implanted portion of the preferred visual prosthesis showing the strap fan tail in more detail.

FIGS. 7 and 8 present the general structure of a visual prosthesis used in implementing the invention.

FIG. 7 shows a perspective view of the implanted portion of the preferred visual prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The secondary inductive coil receives power and data from a primary inductive coil 17, which is external to the body. The electronics package 14 and secondary inductive coil 16 are held together by the molded body 18. The molded body 18 holds the electronics package 14 and secondary inductive coil 16 end to end. The secondary inductive coil 16 is placed around the electronics package 14 in the molded body 18. The molded body 18 holds the secondary inductive coil 16 and electronics package 14 in the end to end orientation and minimizes the thickness or height above the sclera of the entire device. The molded body 18 may also include suture tabs 20. The molded body 18 narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

FIG. 8 shows a side view of the implanted portion of the visual prosthesis, in particular, emphasizing the fan tail 24. When implanting the visual prosthesis, it is necessary to pass the strap 22 under the eye muscles to surround the sclera. The secondary inductive coil 16 and molded body 18 must also follow the strap 22 under the lateral rectus muscle on the side of the sclera. The implanted portion of the visual prosthesis is very delicate. It is easy to tear the molded body 18 or break wires in the secondary inductive coil 16. In order to allow the molded body 18 to slide smoothly under the lateral rectus muscle, the molded body 18 is shaped in the form of a fan tail 24 on the end opposite the electronics package 14. The strap 22 further includes a hook 28 the aids the surgeon in passing the strap under the rectus muscles.

Referring to FIG. 9, the visual prosthesis system including external components may be used to configure and optimize the visual prosthesis (3) of the Retinal Stimulation System (1).

The visual prosthesis system may comprise custom software with a graphical user interface (GUI) running on a dedicated laptop computer (10). Within the visual prosthesis system are modules for performing diagnostic checks of the implant, loading and executing video configuration files, viewing electrode voltage waveforms, and aiding in conducting psychophysical experiments. A video module can be used to download a video configuration file to a Video Processing Unit (VPU) (20) and store it in non-volatile memory to control various aspects of video configuration, e.g. the spatial relationship between the video input and the electrodes. The software can also load a previously used video configuration file from the VPU (20) for adjustment.

The visual prosthesis system can be connected to the Psychophysical Test System (PTS), located for example on a dedicated laptop (30), in order to run psychophysical experiments. In psychophysics mode, the visual prosthesis system enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB (MathWorks) software and other tools to allow the clinicians to develop customized psychophysics experiment scripts.

Any time stimulation is sent to the VPU (20), the stimulation parameters are checked to ensure that maximum charge per phase limits, charge balance, and power limitations are met before the test stimuli are sent to the VPU (20) to make certain that stimulation is safe.

Using the psychophysics module, important perceptual parameters such as perceptual threshold, maximum comfort level, and spatial location of percepts may be reliably measured.

Based on these perceptual parameters, the fitting software enables custom configuration of the transformation between video image and spatio-temporal electrode stimulation parameters in an effort to optimize the effectiveness of the visual prosthesis for each subject.

The visual prosthesis system laptop (10) is connected to the VPU (20) using an optically isolated serial connection adapter (40). Because it is optically isolated, the serial connection adapter (40) assures that no electric leakage current can flow from the visual prosthesis system laptop (10).

As shown in FIG. 9, the following components may be used with the visual prosthesis system according to the present disclosure. A Video Processing Unit (VPU) (20) for the subject being tested, a Charged Battery (25) for VPU (20), Glasses (5), a visual prosthesis system (FS) Laptop (10), a Psychophysical Test System (PTS) Laptop (30), a PTS CD (not shown), a Communication Adapter (CA) (40), a USB Drive (Security) (not shown), a USB Drive (Transfer) (not shown), a USB Drive (Video Settings) (not shown), a Patient Input Device (RF Tablet) (50), a further Patient Input Device (Jog Dial) (55), Glasses Cable (15), CA-VPU Cable (70), CFS-CA Cable (45), CFS-PTS Cable (46), Four (4) Port USB Hub (47), Mouse (60), LED Test Array (80), Archival USB Drive (49), an Isolation Transformer (not shown), adapter cables (not shown), and an External Monitor (not shown).

The external components of the visual prosthesis system according to the present disclosure may be configured as follows. The battery (25) is connected with the VPU (20). The PTS Laptop (30) is connected to FS Laptop (10) using the CFS-PTS Cable (46). The PTS Laptop (30) and FS Laptop (10) are plugged into the Isolation Transformer (not shown) using the Adapter Cables (not shown). The Isolation Transformer is plugged into the wall outlet. The four (4) Port USB Hub (47) is connected to the FS laptop (10) at the USB port. The mouse (60) and the two Patient Input Devices (50) and (55) are connected to four (4) Port USB Hubs (47). The FS laptop (10) is connected to the Communication Adapter (CA) (40) using the CFS-CA Cable (45). The CA (40) is connected to the VPU (20) using the CA-VPU Cable (70). The Glasses (5) are connected to the VPU (20) using the Glasses Cable (15).

Accordingly, what has been shown is an improved retinal prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

We claim:

1. A method of stimulating visual neurons to create the perception of light comprising:
    providing a visual prosthesis including an array of electrodes suitable to stimulate neural tissue:
    determining a minimum distance at which spatiotemporal interactions occur;
    determining a minimum time at which spatiotemporal interactions occur; and
    avoiding stimulation of electrodes within the minimum distance during the minimum time.

2. The method according to claim 1, wherein the minimum distance is 2 mm.

3. The method according to claim 1, wherein the minimum time is 1.8 msec.

4. A method of stimulating visual neurons to create the perception of light comprising:
    providing a visual prosthesis including an array of electrodes suitable to stimulate neural tissue:
    determining a minimum distance at which spatiotemporal interactions occur;
    determining a minimum time at which spatiotemporal interactions occur; and reducing stimulation of electrodes within the minimum distance during the minimum time according to a predetermined formula.

5. The method according to claim 4, wherein the minimum distance is 2 mm.

6. The method according to claim 4, wherein the minimum time is 1.8 msec.

7. The method according to claim 4, wherein the predetermined formula is $B_\tau = E_1^\beta + E_2^\beta + \gamma_\tau E_1 E_2$.

8. A method of stimulating visual neurons to create the perception of light comprising:
   providing a visual prosthesis including an image source linked to an array of electrodes, suitable to stimulate neural tissue, by a video processor:
   determining a minimum distance at which spatiotemporal interactions occur;
   determining a minimum time at which spatiotemporal interactions occur; and
   altering an image in the video processor when it is determined that without alteration electrodes within the minimum distance will be stimulated within minimum time.

9. The method according to claim 8, wherein the minimum distance is 2 mm.

10. The method according to claim 8, wherein the minimum time is 1.8 msec.

11. The method according to claim 8, wherein the step of altering comprises:
    determining a mean luminance value of a first subset of electrodes;
    determining a mean luminance value for a second subset of electrodes; and
    adjusting luminance values for the second subset of electrodes according to the relationship of the mean luminance value of the first subset of electrodes and the mean luminance value of the second subset of electrodes.

* * * * *